United States Patent [19]

Gupta et al.

[11] Patent Number: 5,629,080
[45] Date of Patent: May 13, 1997

[54] THERMALLY BONDABLE FIBER FOR HIGH STRENGTH NON-WOVEN FABRICS

[75] Inventors: Rakesh K. Gupta; James E. Mallory; Kunihiko Takeuchi, all of Conyers, Ga.

[73] Assignee: Hercules Incorporated, Wilmington, Del.

[21] Appl. No.: 3,696

[22] Filed: Jan. 13, 1993

Related U.S. Application Data

[63] Continuation-in-part of Ser. No. 943,190, Sep. 11, 1992, abandoned, which is a continuation-in-part of Ser. No. 818,772, Jan. 13, 1992, abandoned.

[51] Int. Cl.$^6$ ............................. D04H 1/58; D02G 3/00; C08L 23/04; C08F 255/02
[52] U.S. Cl. .................. 428/373; 428/374; 525/240; 525/319; 525/322; 525/324; 525/935; 442/361
[58] Field of Search .................. 428/288, 296, 428/373, 374; 525/240, 319, 322, 324, 935

[56] References Cited

U.S. PATENT DOCUMENTS

| | | | |
|---|---|---|---|
| 2,335,922 | 12/1943 | Dreyfus | 18/54 |
| 2,715,075 | 8/1955 | Wolinski | 264/83 |
| 2,715,076 | 8/1955 | Wolinski | 264/83 |
| 2,715,077 | 8/1955 | Wolinski | 264/83 |
| 2,904,828 | 9/1959 | Smith | 18/8 |
| 2,985,995 | 5/1961 | Bunting, Jr. et al. | 57/246 |
| 3,067,458 | 12/1962 | Dauchert | 18/8 |
| 3,216,187 | 11/1965 | Chantry et al. | 57/140 |
| 3,353,211 | 11/1967 | Heijnis | 18/8 |
| 3,354,250 | 11/1967 | Killoran et al. | 264/176 |
| 3,361,859 | 1/1968 | Cenzato | 264/176 |
| 3,364,537 | 1/1968 | Bunting, Jr. et al. | 57/333 |
| 3,420,724 | 1/1969 | Saunders | 156/272 |
| 3,428,506 | 2/1969 | Johnstone | 156/148 |
| 3,436,298 | 4/1969 | Oppenlander et al. | 161/150 |
| 3,437,725 | 4/1969 | Pierce | 264/176 |
| 3,484,916 | 12/1969 | Johnstone | 28/72.2 |
| 3,505,164 | 4/1970 | Oppenlander | 161/173 |
| 3,509,013 | 4/1970 | Oppenlander | 161/173 |
| 3,516,899 | 6/1970 | Saunders | 161/148 |
| 3,533,904 | 10/1970 | Jurkiewitsch | 161/173 |
| 3,597,268 | 8/1971 | Smith | 117/138.8 |
| 3,601,846 | 8/1971 | Hudnall | 425/131.5 |
| 3,616,168 | 10/1971 | Johnstone | 161/154 |
| 3,663,675 | 5/1972 | Fukuma et al. | 264/168 |
| 3,693,341 | 9/1972 | Higgins, Jr. | 57/333 |
| 3,807,917 | 4/1974 | Shimoda et al. | 425/131.5 |
| 3,862,265 | 1/1975 | Steinkamp et al. | 425/376 |
| 3,898,209 | 8/1975 | Watson et al. | 264/83 |
| 3,900,678 | 8/1975 | Aishima et al. | 428/374 |
| 3,907,057 | 9/1975 | Reddekopp | 296/38 M |
| 3,907,957 | 9/1975 | Shaffer | 264/237 |
| 4,035,127 | 7/1977 | Ogasawara et al. | 425/378.2 |
| 4,087,485 | 5/1978 | Huff | 260/897 A |
| 4,115,620 | 9/1978 | Gupta et al. | 428/374 |
| 4,134,882 | 1/1979 | Frankfort et al. | 528/309 |
| 4,193,961 | 3/1980 | Roberts | 264/234 |
| 4,195,051 | 3/1980 | Frankfort et al. | 264/210.2 |
| 4,251,200 | 2/1981 | Parkin | 264/171 |
| 4,259,399 | 3/1981 | Hill | 428/288 |
| 4,296,022 | 10/1981 | Hudson | 525/240 |
| 4,303,606 | 12/1981 | Roberts | 264/234 |
| 4,347,206 | 8/1982 | Roberts | 264/234 |
| 4,361,489 | 11/1982 | Kilsdonk | 425/185 |
| 4,438,238 | 3/1984 | Fukushima et al. | 525/240 |
| 4,473,677 | 9/1984 | Pellegrini et al. | 524/109 |
| 4,477,516 | 10/1984 | Sugihara et al. | 428/296 |
| 4,480,000 | 10/1984 | Watanabe et al. | 428/284 |
| 4,500,384 | 2/1985 | Tomioka et al. | 156/296 |
| 4,511,615 | 4/1985 | Ohta | 428/198 |
| 4,521,483 | 6/1985 | Sasaki et al. | 428/373 |
| 4,564,553 | 1/1986 | Pellegrini et al. | 428/296 |
| 4,578,414 | 3/1986 | Sawyer et al. | 524/310 |
| 4,592,943 | 6/1986 | Cancian et al. | 428/171 |
| 4,626,467 | 12/1986 | Hostetter | 428/288 |
| 4,632,861 | 12/1986 | Vassilatos | 428/296 |
| 4,634,739 | 1/1987 | Vassilatos | 525/240 |
| 4,652,484 | 3/1987 | Shiba et al. | 428/286 |
| 4,680,156 | 7/1987 | Collier | 264/327 |
| 4,717,325 | 1/1988 | Fujimura et al. | 264/171 |
| 4,726,976 | 2/1988 | Karami et al. | 428/137 |
| 4,732,809 | 3/1988 | Harris, Jr. et al. | 428/373 |

(List continued on next page.)

FOREIGN PATENT DOCUMENTS

| | | |
|---|---|---|
| 2035575 | 7/1990 | Canada . |
| 0279511 | 8/1988 | European Pat. Off. . |
| 0391438 | 10/1990 | European Pat. Off. . |
| 0445536 | 9/1991 | European Pat. Off. . |
| 4234790 | 4/1993 | Germany . |
| 59-66508 | 4/1984 | Japan . |
| 2041412 | 2/1990 | Japan . |
| 34908 | 1/1957 | Luxembourg . |
| 9208538B | 10/1992 | Rep. of Korea . |
| 738474 | 10/1955 | United Kingdom . |
| 2121423 | 12/1983 | United Kingdom . |
| 2258869 | 2/1993 | United Kingdom . |

OTHER PUBLICATIONS

Legare, 1986 TAPPI Synthetic Fibers For Wet System and Thermal Bonding Applications, Boston Park Plaza Hotel &Towers, Boston, MA, Oct. 9–10, 1986, "Thermal Bonding of Polypropylene Fibers in Nonwovens", pp. 1–13 and attached Tables and Figures.

Kloos, The Plastics and Rubber Institute, The Conference Department, Fouth International Conference On Polypropylene Fibers And Textiles, East Midlands Conference Centre, Nottinghas, London, UK: Wednesday 23 to Friday 25 Sep. 1987, "Dependence of Structure and Properties of Melt Spun Polypropylene Fibers on Molecular Weight Distribution, pp. i and 6/1–6/10".

(List continued on next page.)

*Primary Examiner*—Thurman K. Page
*Assistant Examiner*—Kathryne E. Shelborne
*Attorney, Agent, or Firm*—Mark D. Kuller

[57] ABSTRACT

Thermobondable fiber of at least one first component of polypropylene having a melt flow rate of 0.5–30, and at least one second component of polypropylene having a melt flow rate of 60–1000.

117 Claims, No Drawings

U.S. PATENT DOCUMENTS

| | | | |
|---|---|---|---|
| 4,770,925 | 9/1988 | Uchikawa et al. | 428/219 |
| 4,789,592 | 12/1988 | Taniguchi et al. | 428/373 |
| 4,795,668 | 1/1989 | Krueger et al. | 428/174 |
| 4,798,757 | 1/1989 | Modrak et al. | 428/286 |
| 4,804,577 | 2/1989 | Hazelton et al. | 428/224 |
| 4,818,587 | 4/1989 | Ejima et al. | 428/198 |
| 4,828,911 | 5/1989 | Morman | 428/288 |
| 4,830,904 | 5/1989 | Gessner et al. | 428/219 |
| 4,837,078 | 6/1989 | Harrington | 428/284 |
| 4,840,846 | 6/1989 | Ejima et al. | 428/373 |
| 4,840,847 | 6/1989 | Ohmae et al. | 428/373 |
| 4,842,922 | 6/1989 | Krupp et al. | 428/296 |
| 4,851,284 | 7/1989 | Yamanoi et al. | 428/284 |
| 4,868,031 | 9/1989 | Modrak et al. | 428/198 |
| 4,874,666 | 10/1989 | Kubo et al. | 428/398 |
| 4,883,707 | 11/1989 | Newkirk | 428/219 |
| 4,909,976 | 3/1990 | Cuculo et al. | 264/211 |
| 4,921,607 | 5/1990 | Langley | 425/199 |
| 4,938,832 | 7/1990 | Schmalz | 428/290 |
| 4,997,875 | 3/1991 | Geddes et al. | 524/504 |
| 5,009,951 | 4/1991 | Ohmae et al. | 428/294 |
| 5,015,694 | 5/1991 | Milani et al. | 525/240 |
| 5,025,124 | 6/1991 | Alfredeen | 219/673 |
| 5,033,172 | 7/1991 | Harrington | 156/62.4 |
| 5,045,387 | 9/1991 | Schmalz | 428/284 |
| 5,066,723 | 11/1991 | Randall, Jr. et al. | 525/194 |
| 5,082,720 | 1/1992 | Hayes | 428/224 |
| 5,130,196 | 7/1992 | Nishio et al. | 428/373 |
| 5,133,917 | 7/1992 | Jezic et al. | 428/373 |
| 5,143,779 | 9/1992 | Newkirk et al. | 428/218 |
| 5,266,392 | 11/1993 | Land et al. | 428/224 |
| 5,272,003 | 12/1993 | Peacock | 428/357 |
| 5,277,974 | 1/1994 | Kubo et al. | 428/373 |
| 5,281,378 | 1/1994 | Kozulla | 264/83 |
| 5,294,482 | 3/1994 | Gessner | 428/287 |
| 5,318,735 | 6/1994 | Kozulla | 264/83 |
| 5,336,552 | 8/1994 | Strack et al. | 428/224 |
| 5,372,885 | 12/1994 | Tabor et al. | 428/373 |
| 5,431,994 | 7/1995 | Kozulla | 428/288 |

OTHER PUBLICATIONS

Durcova et al., "Structure of Photoxidized Polypropylene Fibers", *Polymer Science U.S.S.R.*, vol. 29, No. 10 (1987), pp. 2351–2357.

Fan et al., "Effects of Molecular Weight Distribution on the Melt Spinning of Polypropylene Fibers", *Journal of Polymer Engineering*, vol. 5, No. 2 (1985) pp. 95–123.

Jeffries, R. "Biocomponent Fibers", Morrow Monograph Publ. Co., 71.

Jones, The Plastics and Rubber Institute, The Conference Department, Fourth International Conference on Polypropylene Fibers and Textiles, East Midlands Conference Centre, Nottinghas, London, UK: Wednesday 23 to Friday 25 Sep. 1987, "A Study of Resin Melt Flow Rate and Polydispersity Effects on the Mechanical Properties of Melt Blown Polypropylene Webs", pp. i and 46/1–46/10.

Mahajan et al.,"Fibers Spun From Blends of Different Molecular Weights of Polypropylene", *Journal of Applied Polymer Science*, vol. 43, 49–56 (1991).

Seiler and Goller, "Propylene (PP)" *Kunststoffe* 80 (1990) 10, pp. 1085–1092.

Trent et al., "Ruthenium Tetroxide Staining of Polymers for Election Microscopy" *Macromolecules*, vol. 16. No. 4, 1983.

Zeichner and Patel, *Proceedings of Second World Congress of Chemical Engineering, Montreal*, vol. 6 (1981) pp. 333–337.

Jeffries, R., "Bicomponent Fibres", Merrow Monograph Publ. Co., Ltd., 1971, pp. v & 1–70.

English Language abstract of Japanese Patent 48–018519 to Sekisui Chem. Co. Ltd.

English Language abstract of Japanese Patent 63–061038 to Mitsubishi Petrochemical K.K.

English Language abstract of Japanese Patent 63–168445 to Chisso Corp.

English Language abstract of Japanese Patent 3–092416 to Daiwa Spinning K.K.

Deopura et al., "A Study of Blends of Different Molecular Weights of Polypropylene" *Journal of Applied Polymer Science*, vol. 31, 2145–2155 (1986).

M. Jambrich et al., Faserforschung und Textiltechnik 18 (1967); Heft 2, pp. 103–107, with English translation.

M. Compostella et al., Angew. Chem, 74, Nr. 16, 1962, pp. 618–624, with English translation.

Derwent Abstract No. WPI ACC No. 73–13421U/10 of SU 326142.

English Abstract of JP 63–168445 to Chisso Corp.

Patent Abstracts of Japan, vol. 008, No. 168 (C–236), Aug. 3, 1984.

Patent Abstracts of Japan, vol. 012, No. 326 (C–525), Sep. 5, 1988.

Patent Abstracts of Japan, vol. 012, No. 338 (C–527), Sep. 12, 1988.

Derwent Abstract No. WPI Acc. No: 84–130971/21.

Derwent Abstract No. WPI Acc. No: 88–151595/22.

Derwent Abstract No. WPI Acc. No: 88–158496/23.

Olivieri et al., The Plastics and Rubber Institute, The Conference Department, Fourth International Conference on Polypropylene Fibres and Textiles, East Midlands Conference Centre, Nottinghas, London, UK: Wednesday 23 to Friday 25 Sep. 1987, "Thermal Bonding —The Fastest–Growing Application for Polypropylene Staple: Success and Development", pp. 40/1–40/10.

Catalyst Consultants, Inc., A Select Client Study "Technical Advances in Reactive Processing for Polymer Blends/Alloys Production 1990–2000", Apr. 1990, pp. 1–7.

Tzoganakis et al., Polymer Engineering and Science, Mar. 1989, vol. 29, No. 6, pp. 390–396, "Effect of Molecular Weight Distribution on the Rheological And Mechanical Properties of Polypropylene".

Prost et al., Makromol. Chem. Macromol. Symp., 23, 173–182 (1989), "Influence of Molecular Weight and Spinning Conditions on the Cystalline Morphology of Polypropylene Fibres".

Yamane et al., Polymer Engineering and Science, Jun. 1993, 1983, vol. 23, No. 9, pp. 516–520, "Extrusion and Melt Spinning Characteristics of Thermally Degraded Polypropylene".

Lu et al., Journal of Applied Polymer Science, vol. 34, 1521–1539 (1987), "The Influence of Resin Characteristics on the High Speed Melt Spinning of Isotactic Polypropylene. I. Effect of Molecular Weight and Its Distribution on Structure and Mechanical Properties of As–Spun Filaments".

Lu et al., Journal of Applied Polymer Science, vol. 34, 1541–1556 (1987), "The Influence of Resin Characteristics on the High Speed Melt Spinning of Isotactic Polypropylene. II. On–Line Studies of Diameter, Birefringence, and Temperature Profiles".

McDonald et al. *Fiber Producer*, Aug. 1983, pp. 38–66.

Krag, The Plastics and Rubber Institute, The Conference Department, Fourth International Conference on Polypropylene Fibres and Textiles, East Midlands Conference Centre, Nottinghas, London, UK: Wednesday 23 to Friday 25 Sep. 1987, "Nonwoven Properties in Relation to Fibre Characteristics", pp. 39/1–39/9.

Ross, Journal of Applied Polymer Science, vol. 9, pp. 2729–2748 (1965).

Abridgement of Israeli patent No. 90437 and claims.

Abridgement of Israeli patent No. 95740 and claims.

Israeli Office Action.

THERMALLY BONDABLE FIBER FOR HIGH STRENGTH NON-WOVEN FABRICS

This application is a continuation-in-part of application Ser. No. 07/943,190, filed Sep. 11, 1992, now abandoned, which is a continuation-in-part of application Ser. No. 07/818,772, filed Jan. 13, 1992, now abandoned the disclosures of which are hereby incorporated by reference in their entirety.

CROSS-REFERENCE TO RELATED APPLICATIONS

This application is related to application Ser. No. 07/474,897, filed Feb. 5, 1990, now abandoned, in the name of Kozulla, its continuation application Ser. No. 07/887,416, filed May 20, 1992, now U.S. Pat. No. 5,281,378, its continuation-in-part application Ser. No. 07/683,635, filed Apr. 11, 1991, now U.S. Pat. No. 5,318,735, and its divisional application Ser. No. 07/836,438, filed Feb. 18, 1992, now abandoned, and its continuation application Ser. No. 07/939,857, filed Sep. 2, 1992, now U.S. Pat. No. 5,431,994, the disclosures of which are hereby incorporated by reference in their entirety.

BACKGROUND OF THE INVENTION

1. Field of the Invention

The present invention relates to synthetic fibers used in the manufacture of non-woven fabrics. In particular, the present invention relates to polypropylene fibers intended for such use, processes of producing polypropylene fibers, compositions for producing polypropylene fibers, non-woven fabrics produced with polypropylene fibers, and articles containing polypropylene fibers.

2. Background Information

The production of polypropylene fibers and filaments usually involves the use of a mix of a single polymer with nominal amounts of stabilizers and pigments. The mix is melt extruded into fibers and fibrous products using conventional commercial processes. Non-woven fabrics are typically made by making a web of the fibers, and then thermally bonding the fibers together where they meet. More specifically, staple fibers are converted into non-woven fabrics using, for example, a carding machine, and the carded fabric is thermally bonded. The thermal bonding can be achieved using various heating techniques, including heating with heated rollers and heating through the use of ultrasonic welding.

Conventional thermally bonded non-woven fabrics exhibit good loft and softness properties, but less than optimal cross-directional strength, and less than optimal cross-directional strength in combination with high elongation. The strength of the thermally bonded non-woven fabrics depends upon the orientation of the fibers and the inherent strength of the bond points.

Over the years, improvements have been made in fibers which provide stronger bond strengths. However, further improvements are needed to provide even higher fabric strengths to permit use of these fabrics in today's high speed converting processes for hygiene products, such as diapers and other types of incontinence products. In particular, there is a need for a thermally bondable fiber and a resulting nonwoven fabric that possess high cross-directional strength and high elongation. Additionally, there is a need for a one-step process for making staple fiber known as a "short spin" process that provides filaments and fibers with properties as good as those produced by a two-step process called a "long spin" process.

SUMMARY OF THE INVENTION

Accordingly, it is an object of the present invention to provide a thermally bondable fiber and a resulting nonwoven fabric that possesses high cross directional strength and high elongation. Additionally, it is an object of the present invention to provide a "short spin" process that provides filaments and fibers that have properties that have qualities that are as good as those produced by a "long spin" process.

The object of the present invention is achieved by providing a fiber comprising at least one polypropylene having a melt flow rate of about 0.5–30, and at least one polypropylene having a melt flow rate of about 60–1000.

Preferably, based on the weight of the fiber, the fiber comprises at least about 3.0% by weight of the at least one polypropylene having a melt flow rate of about 0.5–30, and at least about 3.0% by weight of the at least one polypropylene having a melt flow rate of about 60–1000. More preferably, based on the weight of the fiber, the fiber comprises at least about 10.0% by weight of the at least one polypropylene having a melt flow rate of about 0.5–30, and at least about 10.0% by weight of the at least one polypropylene having a melt flow rate of about 60–1000. Preferably, the fiber comprises at least one polypropylene having a melt flow rate of about 1–25, and at least one polypropylene having a melt flow rate of about 200–1000.

Preferably, based on the weight of the fiber, the at least one polypropylene having a melt flow rate of about 0.5–30 is present in an amount of about 5–95%, and the at least one polypropylene having a melt flow rate of about 60–1000 is present in an amount of about 5–95%. More preferably, the fiber comprises about 2–5% by weight, preferably about 3% by weight, of polypropylene having a melt flow rate of about 0.5–5, preferably about 0.8–5.0, and more preferably about 1.0–3.0, about 70–85% by weight, preferably about 75% by weight, of polypropylene having a melt flow rate of about 10–20, preferably about 10–15, and about 10–28% by weight, preferably about 22% by weight, of polypropylene having a melt flow rate of about 300–600, preferably about 350–450.

The fiber according to the present invention has an average rheological polydispersity index of at least about 4.5, preferably at least about 5.0, more preferably about 5.5, and a preferred range of about 5.0–7.0. Further, the fiber has a viscoelastic constant of about 1.5–2.0, a fiber elongation of at least about 250%, a fiber tenacity less than about 2.5 g/denier, and a size less than about 5 dpf. As utilized in this application dpf denotes denier per filament, with denier being defined as weight in grams per 9,000 meter length of filament.

The fiber can contain at least one additive, and the at least one additive can comprise at least one stabilizer.

It is an additional object of the present invention to provide a composition comprising at least one polypropylene having a melt flow rate of about 0.5–30, preferably, about 1–25, and at least one polypropylene having a melt flow rate of about 60–1000, preferably, about 200–1000. This composition can contain similar components and have similar characteristics as the above-described fiber. For example, the composition can have an average rheological polydispersity index of at least about 4.5, preferably of at least about 5.0, more preferably at least about 5.5, and a preferred range of about 5.0–7.0, and can contain at least one additive, such as at least one stabilizer.

Also, the composition can comprise, based on the weight of the composition, at least one polypropylene having a melt flow rate of about 0.5–30 present in an amount of about 5–95%, and at least one polypropylene having a melt flow rate of about 60–1000 is present in an amount of about 5–95%. Preferably, based on the weight of the composition, the composition comprises at least about 3.0% by weight of the at least one polypropylene having a melt flow rate of about 0.5–30, and at least about 3.0% by weight of the at least one polypropylene having a melt flow rate of about 60–1000. More preferably, based on the weight of the composition, the composition comprises at least about 10.0% by weight of the at least one polypropylene having a melt flow rate of about 0.5–30, and at least about 10.0% by weight of the at least one polypropylene having a melt flow rate of about 60–1000.

Preferably, the composition comprises about 2–5% by weight, preferably about 3% by weight of polypropylene having a melt flow rate of about 0.5–5, preferably about 0.8–5, and more preferably about 1.0–3.0, about 70–85% by weight, preferably about 75% by weight, of polypropylene having a melt flow rate of about 10–20, preferably about 10–15, and about 10–28% by weight, preferably about 22% by weight, of polypropylene having a melt flow rate of about 300–600, preferably about 350–450.

It is also an object of the present invention to provide a polypropylene containing fiber comprising a mixture of at least two components, the at least two components comprising at least one first component of polypropylene having a melt flow rate of about 0.5–30, and at least one second component of polypropylene having a melt flow rate of about 60–1000, preferably about 200–1000, and the fiber having an average melt flow rate of about 5–40, preferably about 10–30, and more preferably about 15–25.

It is also an object of the present invention to provide a polypropylene containing fiber having an average melt flow rate of about 5–40, preferably 10–30 and more preferably about 15–25, and containing at least about 3.0% of at least one polypropylene having a melt flow rate of about 200–1000, and preferably containing at least about 10% of the at least one polypropylene having a melt flow rate of about 200–1000.

It is also an object of the present invention to provide a polypropylene containing fiber having an average rheological polydispersity index of at least about 4.5, preferably of at least about 5.0, more preferably of at least about 5.5, and a preferred ranged of about 5.0 to 7.0, and containing at least about 3.0% of at least one polypropylene having a melt flow rate of about 200–1000, and preferably containing at least about 10% of the at least one polypropylene having a melt flow rate of about 200–1000. Preferably, the polypropylene containing fiber has an average melt flow rate of about 5–40, more preferably about 10–30, and most preferably about 15–25.

It is yet another object of the present invention to provide a thermobondable polypropylene fiber, the fiber comprising components having a zero shear viscosity of at least about $2.0 \times 10^4$ poise, and a viscoelastic constant of at least about 1.5.

The present invention is also directed to a thermally bondable fiber, the fiber having an average rheological polydispersity index of at least about 5.0, preferably of at least about 5.5, and a preferred range of about 5.0–7.0.

The thermobondable polypropylene fiber according to present invention as above-described in each of its different aspects has a substantially uniform morphology. This substantially uniform morphology is demonstratable by the above-described fibers being substantially uniformly stainable with ruthenium tetroxide.

Still further, it is an object of the present invention to provide a process for spinning polypropylene containing filaments comprising melt spinning a polypropylene composition having a broad molecular weight distribution through at least one spinnerette to form molten polypropylene containing filaments; and quenching the molten polypropylene containing filaments to obtain polypropylene containing filaments having an average rheological polydispersity index of at least about 5.0, preferably of at least about 5.5, and a preferred range of about 5.0–7.0. The spinning speed can be about 30 to 200 meters per minute, preferably about 80–100 meters per minute, and the polypropylene containing filaments can be continuously drawn and crimped, as practiced with a "short spin; process. Alternatively, the spinning speed can be about 500 to 2500 meters per minute, preferably about 1100–2000 meters per minute, and the polypropylene containing filaments can be drawn and crimped at a speed of about 50 to 250 meters per minute, preferably about 150–200 meters per minute, in a second step, as practiced with a "long spin" process.

The quenching according to the process according to the present invention can be effected to obtain a substantially immediate cooling of the molten polypropylene containing filaments as the molten polypropylene containing filaments exit the at least one spinnerette. Preferably, the quench comprises an air quench having a velocity, for a "short spin" process, of about 10–45 meters/second, preferably about 25–35 meters/second, and more preferably about 30 meters/second; and, for a "long spin" process, of about 1.5–4.0 meters/second, preferably about 2.0 meters/second. The quench air temperature is about 10°–40° C., preferably about 15°–30° C., and more preferably either about 15°–20° C. or about 37° C.

Still further, it is an object of the present invention to provide a process for spinning polypropylene containing filaments comprising melt spinning a polypropylene containing composition having a broad molecular weight distribution through at least one spinnerette at a spinning speed of about 30 to 200 meters per minute, preferably about 80–100 meters per minute, to form molten polypropylene containing filaments; and quenching the molten polypropylene containing filaments. Preferably, the quenched filaments have an average rheological polydispersity index of at least about 4.5, more preferably of at least about 5.0, even more preferably of at least about 5.5, and a preferred range of 5.0–7.0. Preferably, the polypropylene containing composition comprises at least one polypropylene having a melt flow rate of about 0.5–30, and at least one polypropylene having a melt flow rate of about 60–1000.

Still further, the present invention is directed to a process for producing thermobondable filaments having an average rheological polydispersity index of at least about 4.5, preferably at least about 5.0, and more preferably about 5.0–7.0 which is substantially maintained throughout the process, comprising melt spinning a polypropylene containing composition having a broad molecular weight distribution with an average rheological polydispersity index of at least about 4.5, preferably of at least about 5.0, more preferably of at least about 5.5, and a preferred range of about 5.0–7.0, through at least one spinnerette to form molten polypropylene filaments; and quenching the molten polypropylene filaments under conditions to obtain filaments having an average rheological polydispersity index substantially corresponding to the rheological polydispersity index of the polypropylene containing composition. This process can use the spinning speeds, drawing and crimping, and quenching steps as described throughout the disclosure.

Still further, the present invention is directed to a process for producing thermobondable filaments having an average rheological polydispersity index of at least about 4.5, preferably of at least about 5.0, more preferably of at least about 5.5, and a preferred range of about 5.0–7.0, which is substantially maintained throughout the process, comprising melt spinning a polypropylene containing composition having a broad molecular weight distribution through at least one spinnerette to form molten polypropylene containing filaments; and quenching the molten polypropylene containing filaments under conditions to maintain a substantially uniform morphology of the quenched polypropylene containing filaments having an average rheological polydispersity index substantially corresponding to the rheological polydispersity index of the polypropylene containing composition. This process can again use the spinning speeds, drawing and crimping, and quenching steps as previously described.

Still further, it is an object of the present invention to provide a process for spinning polypropylene containing filaments comprising melt spinning a polypropylene containing composition having a broad molecular weight distribution through at least one spinnerette at a spinning speed of about 30 to 200 meters per minute, preferably 80 to 100 meters per minute, to form molten polypropylene containing filaments; and quenching the molten polypropylene containing filaments to obtain polypropylene containing filaments having an average theological polydispersity index of at least about 4.5, preferably of at least about 5.0, more preferably of at least about 5.5. Preferably, the filaments have an elongation greater than about 250%. Further, the polypropylene containing composition preferably contains at least about 3.0%, preferably at least about 10.0%, of at least one polypropylene having a melt flow rate of about 60–1000, preferably of about 200–1000. Preferably, the filaments have an average melt flow rate of about 5–40, more preferably an average melt flow rate of about 10–30, and most preferably an average melt flow rate of about 15–25.

Still further, it is an object of the present invention to provide a process for spinning polypropylene containing filaments comprising melt spinning a polypropylene containing composition having a broad molecular weight distribution, and containing at least about 3.0%, preferably at least about 10.0%, of at least one polypropylene having a melt flow rate of about 60–1000, preferably a melt flow rate of about 200–1000, through at least one spinnerette at a spinning speed of about 30 to 200 meters per minute, preferably of about 80–100 meters per minute, to form molten polypropylene containing filaments; and quenching the molten polypropylene containing filaments to obtain polypropylene containing filaments having an average melt flow rate of about 5–40. Preferably, the filaments have an average rheological polydispersity index is at least about 4.5, more preferably of at least about 5.0, even more preferably of at least about 5.5, and an elongation greater than about 250%.

It is also an object of the present invention to provide non-woven material comprising fibers as described above that are thermally bonded together; and to provide products having at least one layer of a non-woven material according to the present invention; and to provide hygienic products, including diapers, incontinence products and sanitary napkins, comprising at least one absorbent layer, and at least one nonwoven fabric comprising nonwoven material of the invention and fibers as above-described thermally bonded together. Further, articles according to the present invention can include at least one liquid impermeable layer. For example, the diaper according to the present invention can include an outer impermeable layer, an inner nonwoven fabric layer comprising fibers according to the present invention, and an intermediate absorbent layer.

Still further, it is an object of the present invention to provide a nonwoven material comprising polypropylene containing fibers having an average melt flow rate of about 5–40, preferably about 10–30, more preferably about 15–25, and containing at least about 3.0%, preferably at least about 10.0%, of at least one polypropylene having a melt flow rate of about 60–1000, preferably a melt flow rate of about 200–1000, thermally bonded together.

Still further, it is an object of the present invention to provide a nonwoven material comprising polypropylene containing fibers having an average rheological polydispersity index of at least about 4.5, preferably about 5.0, more preferably about 5.5, and a preferred range of about 5.0–7.0, and containing at least about 3.0%, preferably at least about 10.0%, of at least one polypropylene having a melt flow rate of about 60–1000, preferably having a melt flow rate of about 200–1000, thermally bonded together. Preferably, the polypropylene containing fiber has an average melt flow rate of about 5–40, more preferably about 10–30, and most preferably about 15–25.

Because the fiber of the present invention provides superior bond strength compared with conventional polypropylene fiber, the nonwoven material thus produced exhibits superior cross-directional tensile properties. Further, nonwoven material produced with the fiber of the present invention has superior elongation, uniformity, loftiness, white coloration and softness, while exhibiting the above-noted superior mechanical properties.

DETAILED DESCRIPTION OF THE
PREFERRED EMBODIMENTS

As used herein, polypropylene is utilized in its ordinary commercial meaning wherein the polypropylene is a substantially linear molecule. Further, as used herein, a polypropylene composition includes a material which contains a broad molecular weight distribution of linear polypropylene to enable the obtaining of fibers and filaments which have superior spinning and thermal bonding characteristics. Moreover, the fibers and filaments of the present invention provide non-woven materials of exceptional cross-directional strength, elongation, uniformity, loftiness and softness, by utilizing the disclosed polypropylene compositions including the disclosed linear polypropylene components having a broad molecular weight distribution, whether or not other components are present therein. Further, as used herein, polypropylene includes homopolymers of propylene, various polymers containing propylene, such as copolymers and terpolymers of propylene, and polypropylene mixtures (including blends and alloys produced by mixing separate batches or forming a blend in situ) with other substances and polymers. For example, the polymer can comprise copolymers of propylene, and these copolymers can contain various components. Preferably, such copolymers include up to about 10 weight % of at least one of ethylene and butene, but can contain varying amounts thereof depending upon the desired fiber or filament.

By practicing the process of the present invention, utilizing spin compositions according to the present invention, fibers and filaments can be obtained which have superior spinning and thermal bonding characteristics. Moreover, the fibers and filaments of the present invention provide nonwoven materials of exceptional cross-directional strength, elongation, uniformity, loftiness and softness, by utilizing a material which contains a broad molecular weight distribution of linear polypropylene, whether or not other components are present therein.

The present invention is directed to various forms of fibers, including filaments and staple fibers. These terms are used in their ordinary commercial meanings. Typically, herein, filaments is used to refer to the continuous fiber on the spinning machine. "Staple fiber" is used to refer to cut fibers or filaments. Preferably, for instance, staple fibers for nonwoven fabrics useful in diapers have lengths of about 1 to 3 inches, more preferably 1.25 to 2 inches.

The polypropylene from which the improved fiber of the present invention can be produced includes at least one polypropylene having a melt flow rate of about 0.5–30, preferably about 1–25, and at least one polypropylene having a melt flow rate of about 60–1000, preferably about 200–1000. Preferably, based on the weight of the composition, the at least one polypropylene having a melt flow rate of about 0.5–30 is present in an amount of about 5–95%, and the at least one polypropylene having a melt flow rate of about 60–1000 is present in an amount of about 5–95%.

Preferably, based on the weight of the composition, the composition comprises at least about 3.0% by weight of the at least one polypropylene having a melt flow rate of about 0.5–30, and at least about 3.0% by weight of the at least one polypropylene having a melt flow rate of about 60–1000. More preferably, based on the weight of the composition, the composition comprises at least about 10.0% by weight of the at least one polypropylene having a melt flow rate of about 0.5–30, and at least about 10.0% by weight of the at least one polypropylene having a melt flow rate of about 60–1000.

More preferably, the composition comprises about 2–5% by weight, preferably, about 3% by weight of polypropylene having a melt flow rate of about 0.5–5, preferably about 0.8–5.0, and more preferably about 1.0–3.0, about 70–85% by weight, preferably about 75% by weight, of polypropylene having a melt flow rate of about 10–20, preferably about 10–15, and about 10–28% by weight, preferably about 22% by weight of polypropylene having a melt flow rate of about 300–600, preferably about 350–450.

In a particular embodiment of the invention, the polypropylene fiber can be made by blending at least one polypropylene having a melt flow rate of about 0.5–30, preferably about 1–25, and at least one polypropylene having a melt flow rate of about 60–1000, preferably about 200–1000 to form a composition, and then melt spinning the composition according to known procedures. The melt flow rate (MFR) as described herein is determined according to ASTM D-1238 (condition L;230/2.16).

The polypropylene to be made into fibers can comprise mixtures of more than one polypropylene within each defined MFR range. The melt flow rate of the mixture used to make the fiber of the present invention, as well as the fiber itself, has an average melt flow rate of about 5–40, preferably about 10–30, and more preferably about 15–25.

While the polypropylenes can be blended to obtain a broad mixture of molecular weights in the polypropylene to be produced into fibers, as an alternative to blending separate polymers to obtain the unique composition of the present invention, the components of the propylene to be produced into fibers can be made in situ by polymerizing propylene with or without ethylene or butane by known multi-reactor procedures, such as disclosed in Seiler and Goller, "Polyproplene (PP)," *KUNSTSTOFFE* 80 (1990) 10, pages 1085–1092, the disclosure of which is incorporated herein by reference.

Known processes for making staple fiber include a conventional "two-step long spin" process or "one-step short spin" process. The long spin process involves first melt-extruding fibers at typical spinning speeds of 500 to 1500 meters per minute. Typically, in a second step run at 100 to 250 meters per minute, these fibers are then drawn, crimped, and cut into staple fiber. The one-step short spin process involves conversion from polymer to staple fibers in a single step where typical spinning speeds are in the range of 50 to 200 meters per minute. The productivity of the one-step process is increased with the use of about 5 to 20 times the number of holes in the spinnerette compared to that typically used in the long spin process. For example, spinnerettes for a typical "long spin" process would include approximately 50–4,000, preferably approximately 3,000–3,500 holes, and spinnerettes for a typical "short spin" process would include approximately 4,000 to 100,000 holes preferably, about 30,000–70,000. Typical temperatures for extrusion of the spin melt are about 250°–300° C.

Other means of production of fibrous products include well known melt spun and melt blown processes, which provide continuous filaments-based non-woven fabrics and micro-denier staple-based non-woven fabrics, respectively. The fiber according to the present invention includes the long filamentous fibers made according to well known spun bond processes, as well as staple fibers made by the aforementioned short spin and long spin processes.

The fiber of the present invention has a preferable denier per filament (dpf) of no greater than about 5.0, preferably between about 0.5 and 3.0.

In making the fiber in accordance with the present invention, at least one stabilizer (including antioxidants) is preferably mixed with the polypropylene to be made into a fiber in an amount ranging from about 0.02–1.0 fiber-weight %, preferably about 0.05–0.2 fiber-weight %, in order to prevent deterioration of the fiber after production. Such stabilizers are well known in polypropylene-fiber manufacture and include phenylphosphites (available from General Electric Co. under the name ULTRANOX 626, and from Sandoz Chemical Co. under the name SANDOSTAB PEP-Q), N,N'-bis-piperidinyl diamine-containing materials (available from Ciba Geigy Corp. under the names CHIMASSORB 119 and CHIMASSORB 944), and hindered phenolics (available under the names CYANOX 1790 from American Cyanamid Co. and IRGANOX 1076 from Ciba Geigy Corp.) The at least one stabilizer can be mixed into the blend of polypropylenes, or can be separately added to polypropylenes that are to be mixed together to form a blend to be produced into fibers.

Optionally, whiteners, such as titanium dioxide, in amounts up to about 2 fiber-weight %, antiacids such as calcium stearate, in amounts ranging from about 0.05–0.2 fiber-weight %, colorants, in amounts ranging from 0.01–2.0%, and other well known additives are included in the fiber of the present invention. Wetting agents, such as disclosed in U.S. Pat. No. 4,578,414, incorporated herein by reference, are also usefully incorporated into the fiber of the present invention. Other commercially available useful additives include IRGAFOS 168 (available from American Cyanamid Co.), and LUPERSOL 101 (available from Pennwalt Corp.)

In making the fiber of the present invention, the polypropylene to be made into a fiber preferably includes about 5-95 fiber-weight % of polypropylene having a melt flow rate of about 0.5-30, and about 5-95 fiber weight % polypropylene having a melt flow rate of about 60-1000. Preferably, based on the weight of the composition, the at least one polypropylene having a melt flow rate of about 0.5-30 is present in an amount of about 5-95%, and the at least one polypropylene having a melt flow rate of about 60-1000 is present in an amount of about 5-95%. More preferably, the composition comprises about 2-5% by weight, preferably, about 3% by weight, of polypropylene having a melt flow rate of about 0.5-5, preferably about 0.8-5.0, more preferably about 1.0-3.0, about 70-85% by weight, preferably 75% by weight, of polypropylene having a melt flow rate of about 10-20, preferably about 10-15, and about 10-28% by weight, preferably about 22% by weight of polypropylene having a melt flow rate of about 300-600, preferably about 400.

Preferably, the fiber made in accordance with the present invention has an average rheological polydispersity index (PI) of at least about 4.5, preferably at least about 5.0, and more preferably between about 5.0 and 7.0 as measured according to Zeichner and Patel, *Proceedings of Second World Congress of Chemical Engineering, Montreal*, Vol. 6, pp. 333-337 (1981), incorporated herein by reference. In accordance with this reference, the dynamic shear property of a small polymeric sample subjected to a small amplitude oscillatory motion. The sample is held between two parallel plates of 25 millimeters in diameter at a gap of two millimeters. The top plate is attached to a dynamic motor while the bottom plate is attached to a 2000 gm-cm torque transducer of a Rheometrics®Dynamic Spectrometer or Analyzer. The test temperature is held at 200° C. While keeping the bottom plate stationary, a small amplitude oscillatory motion is imposed on the top plate sweeping the frequency range from 0.1 to 500 radian/second. At each frequency, after the transients have died out, the dynamic stress response is separable into in-phase and out-of-phase components of the shearing strain. The dynamic modulus, G', characterizes the in-phase component while the loss modulus, G", characterizes the out-of-phase component of the dynamic stress. For high molecular weight polyolefins, such as polypropylenes, it is observed that these moduli crossover at a point when measured as a function of frequency. This crossover modulus is characterized as Gc, and the crossover frequency is characterized by Wc.

The polydispersity index is defined by $10^6$/crossover modulus, and is found to correlate with the molecular weight distribution, Mw/Mn. The crossover frequency correlates inversely with the weight average molecular weight, Mw, for polypropylenes.

Preferably, the fiber of the present invention also has a viscoelastic constant of about 1.5-2.0. The viscoelastic constant (VC) is defined according to the equation $VC = \eta_o/(Gc/Wc)^{1.21}$, where "$\eta_o$" is the zero shear viscosity in poise, and "Gc/Wc" is the ratio of crossover modulus to crossover frequency in poise, that is (dyne)(sec)/cm². The values of Gc and Wc are determined utilizing the dynamic shear procedure described above. However, the zero shear viscosity is determined utilizing a low shear steady shear procedure in which a cone and plate fixture are used as the platens instead of the two parallel plates in the dynamic shear procedure. More specifically, the cone has a cone angle of 0.1 radian, and both the cone and the plate are 25 mm in diameter. The test temperature is held at 200° C., as with the dynamic shear procedure. While maintaining the bottom plate stationary, a constant rotational motion is imposed on the top cone at a constant shear rate. After an elapsed time, the stress measured by the transducer maintains a constant value. The viscosity is computed from this steady stress, and the imposed shear rate. The zero shear viscosity, $\eta_o$, is defined as the viscosity of a high molecular weight polymer in which the viscosity is invariant as a function of shear rate. The zero Shear viscosity is measured by performing the shear sweep from a shear rate of 0.001 sec$^{-1}$ to 3.0 sec$^{-1}$. The zero shear viscosity is obtained in the low shear rate region, and it is the viscosity that has an associated torque greater than 2 gm-cm, and does not vary with shear rate.

The filaments and fibers of the present invention have a substantially uniform structure. This structure is different from the sheath-core differential morphology that is associated with the polypropylene filaments and fibers of the above-referenced Kozulla patent applications, corresponding subject matter of which was laid open on Aug. 6, 1991 in Canadian Laid-Open Patent Application No. 2,035,575.

The substantially uniform morphological structure of the filaments and fibers according to the present invention is characterizable by transmission electron microscopy (TEM) of ruthenium tetroxide (RuO$_4$)-stained fiber thin sections. In this regard, as taught by Trent et al., in *Macromolecules*, Vol. 16, No. 4, 1983, "Ruthenium Tetroxide Staining of Polymers for Electron Microscopy", which is hereby incorporated by reference in its entirety, it is well known that the microphology of polymeric materials is dependent on their heat treatment, composition, and processing, and that, in turn, mechanical properties of these materials such as toughness, impact strength, resilience, fatigue, and fracture strength can be highly sensitive to morphology. Further, this article teaches that transmission electron microscopy is an established technique for the characterization of the structure of heterogeneous polymer systems at a high level of resolution; however, it is often necessary to enhance image contrast for polymers by use of a staining agent. Useful staining agents for polymers are taught to include osmium tetroxide and ruthenium tetroxide. For the staining of the filaments and fibers of the present invention, ruthenium tetroxide is the preferred staining agent.

In the morphological characterization of the present invention, samples of filaments or fibers are stained with aqueous RuO$_4$, such as a 0.5% (by weight) aqueous solution of ruthenium tetroxide obtainable from Polysciences, Inc., overnight at room temperature. (While a liquid stain is utilized in this procedure, staining of the samples with a gaseous stain is also possible.) Stained fibers are embedded in Spurr epoxy resin and cured overnight at 60° C. The embedded stained fibers are then thin sectioned on an ultramicrotome using a diamond knife at room temperature to obtain microtomed sections approximately 80 nm thick, which can be examined on conventional apparatus, such as a Zeiss EM-10 TEM, at 100 kV. Energy dispersive x-ray analysis (EDX) was utilized to confirm that the RuO$_4$ had penetrated completely to the center of the fiber.

Fibers that are produced according to sheath-core differential morphology of the above-referenced Kozulla applications show an enrichment of the ruthenium on the outside surface of the fiber (Ru residue), and on the outer sheath (approximately 1 µm) of the fiber cross-section. Further, the core of these Kozulla fibers show a much lower ruthenium content. In contrast, fibers that are produced according to the present invention have a more uniform distribution of ruthenium across the fiber cross-section than the fiber produced according to the sheath-core differential morphology of Kozulla, and do not illustrate a sheath-core differential morphology.

It is also preferred that the fiber of the present invention have a tenacity no greater than about 2.5 g/denier, and a fiber elongation of at least about 250%, as measured on individual fibers using a FAFEGRAPH tensile tester with a fiber gauge length of about 1.25 cm and an extension rate of about 200%/min (average of 10 fibers tested). Fiber tenacity is defined as the breaking force divided by the denier of the fiber, while fiber elongation is defined as the % elongation to break.

As discussed above, the present invention provides nonwoven materials including the fibers according to the present invention thermally bonded together. By incorporating the fibers of the present invention into nonwoven materials, nonwoven materials of exceptional cross-directional strength and percent elongation can be obtained. These nonwoven materials can be used as at least one layer in various products, including hygienic products, such as sanitary napkins, incontinence products and diapers, comprising at least one liquid absorbent layer and at least one nonwoven material layer of the present invention and/or incorporating fibers of the-present invention thermally bonded together. Further, as previously indicated, the articles according to the present invention can include at least one liquid impermeable layer. For example, a diaper incorporating a nonwoven fabric of the present invention would include, as a preferred embodiment, an outermost impermeable layer, an inner layer of the nonwoven material, and at least one intermediate absorbent layer. Of course, a plurality of nonwoven material layers and absorbent layers can be incorporated in the diaper (or other hygienic product) in various orientations, and a plurality of outer impermeable layers can be included for strength considerations.

In order to more clearly describe the present invention, the following non-limiting examples are provided. All parts and percentages in the examples are by weight unless indicated otherwise.

EXAMPLE 1

Fibers (2.2 dpf) are prepared using the one-step short spin process with an inside-out radial quench system. The spinnerette contains 64,030 holes, each having a diameter of 0.35 mm. Quench air velocity of about 16–30 meters/second and a spinning speed of 75 meters/minute are used. Fibers are crimped at about 8–12 crimps/cm, coated with a 0.4–0.8 fiber-weight % finish mixture of an ethoxylated fatty acid ester and an ethoxylated alcohol phosphate (available from George A. Goulston Co., Inc., Monroe, NC, under the name LUROL PP 912), and cut into 3.8 cm long staple.

The following polymers are used. Polymer I is a homopolymer of propylene having a MFR of 20 and a PI of 4.2. Polymer II is a homopolymer of propylene having a MFR of 10 and a PI of 5.0. Polymer III is a homopolymer of propylene having a MFR of 18 and a PI of 4.6 (PV711 from Himont Canada). Polymer IV is a homopolymer of propylene having a MFR of 400±40 and a PI of 3.5±0.5 (VALTEC HH441 Himont Inc., Wilmington, Del.). Fiber samples A-H are prepared using the formulations and conditions as set forth in the following Table 1. Fiber samples B-F are examples of the present invention, and fiber samples A, G, and H are controls. Additives % are based on fiber weight.

TABLE 1

| Fiber Formulation | Spin Temp. °C.[1] | Draw Temp. °C.[2] |
|---|---|---|
| A polymer I<br>0.1% IRGAFOS 168<br>0.1% calcium stearate<br>0.02% IRGANOX 1076 | 270 | 49/35 |
| B 80% polymer II<br>20% polymer IV<br>0.06% ULTRANOX 626<br>0.05% calcium stearate<br>0.01% IRGANOX 1076 | 270 | 49/32 |
| C 80% polymer II<br>20% polymer IV<br>0.06% ULTRANOX 626<br>0.05% calcium stearate<br>0.01% IRGANOX 1076 | 280 | 51/31 |
| D 90% polymer III<br>10% polymer IV<br>0.06% ULTRANOX 626<br>0.05% calcium stearate<br>0.01% IRGANOX 1076 | 260 | 51/36 |
| E 85% polymer III<br>15% polymer IV<br>0.06% ULTRANOX 626<br>0.05% calcium stearate<br>0.01% IRGANOX 1076 | 260 | 50/36 |
| F 80% polymer II<br>20% polymer IV<br>0.1% IRGAFOS 168<br>0.05% calcium stearate<br>0.01% IRGANOX 1076 | 280 | 51/33 |
| G polymer II<br>0.1% EBS[3]<br>0.01% LUPERSOL 101<br>0.1% IRGAFOS 168<br>0.05% calcium stearate<br>0.01% IRGANOX 1076 | 280 | 49/35 |
| H polymer II<br>0.1% EBS<br>0.01% LUPERSOL 101<br>0.1% IRGAFOS 168<br>0.05% calcium stearate<br>0.01% IRGANOX 1076 | 280 | 49/35 |

[1]Extruder zones temperature.
[2]Feed-roll temperature/draw-roll temperature.
[3]bis-(p-ethylbenzylidene)sorbitol (obtainable from Mitsui Toatsu Chemicals, Japan).

The fiber samples are tested to determine MFR, PI, and % elongation as described hereinabove. Fibers from each sample are then made into a non-woven material (average weight 23.8 g/m$^2$) by thermally bonding a web of the fibers at 75 m/min card bond line speed at a temperature of 150°–180° C. using a calendar roll having diamond bond points with a total bond area of about 20%. Cross-directional (CD) strength of the resulting fabric is determined by testing samples 2.5 cm wide and 12.5 cm long that have been cut in the cross direction of the fabric production. CD strength is expressed in grams of force needed to break the fabric at the extension rate of 12.5 cm/min. Fiber and fabric test results (CD strength being for the fabric) are reported in the following Table 2.

TABLE 2

| Sample | MFR dg/min | P.I. | Draw Ratio | % Elong | CD Strength g/in | Zero Shear Viscosity (10$^4$ Poise) | VC |
|---|---|---|---|---|---|---|---|
| A | 27 | 4.6 | 1.2X | 378 | 565 | 1.07 | 1.56 |
| B | 18 | 5.6 | 1.2X | 413 | 789 | 2.39 | 1.78 |
| C | 18 | 5.7 | 1.2X | 396 | 683 | 2.36 | 1.76 |

TABLE 2-continued

| Sample | MFR dg/min | P.I. | Draw Ratio | % Elong | CD Strength g/in | Zero Shear Viscosity (10⁴ Poise) | VC |
|---|---|---|---|---|---|---|---|
| D | 25 | 4.8 | 1.35X | 347 | 663 | | |
| E | 26 | 4.8 | 1.35X | 409 | 649 | | |
| F | 20 | 5.3 | 1.1X | 324 | 742 | | |
| G | 23 | 3.8 | 1.1X | 330 | 470 | | |
| H | 23 | 4.1 | 1.3X | 304 | 497 | | |

Comparing results for samples B–F with controls A, G, and H demonstrates that the fibers of the present invention exhibit superior fabric strength and thermal bonding properties.

EXAMPLE 2

Fibers (2.2 dpf) are prepared using a one-step spinning process with a cross-blow quench system. Spinnerettes contained 30,500 0.3 mm diameter holes. Quench air velocity is about 30–35 meters per second. The spinning speed is 86 meters/minute and the drawing speed is 103 meters/minute. The fibers are crimped at about 8–12 crimps/cm and cut into 4.8 cm long staple during the same process. Polypropylene polymers III and IV of the Example I are used in these experiments. Fiber samples J and K are prepared using the formulations and conditions as set forth in the following Table 3. Fiber sample K is an example of the present invention, and fiber sample J is a control. Additives % are based on fiber weight.

TABLE 3

| Fiber Formulation | Spin Temp. °C.[1] | Draw Temp. °C.[2] |
|---|---|---|
| J polymer III<br>0.06% CYANOX 1790<br>0.05% calcium stearate<br>0.1% TiO₂<br>0.01% IRGANOX 1076 | 235 | 60/60 |
| K 95% polymer III<br>5% polymer IV<br>0.085% ULTRANOX 626<br>0.07% calcium Stearate<br>0.14% TiO₂<br>0.01% IRGANOX 1076 | 247 | 60/60 |

[1]Extruder zones temperature.
[2]Feed-roll temperature/draw-roll temperature.

The fiber samples are tested and fabrics made and tested as in Example 1. Results are reported in the following Table 4. Again the CD strength pertains to the fabric and the other results pertain to the fiber.

TABLE 4

| Sample | MFR dg/min | P.I. | Draw Ratio | % Elong | CD Strength g/in | Zero Shear Viscosity (10⁴ Poise) | VC |
|---|---|---|---|---|---|---|---|
| J | 22 | 4.3 | 1.2X | 344 | 600 | 1.35 | 1.58 |
| K | 21 | 4.7 | 1.2X | 376 | 660 | 1.56 | 1.68 |

Sample K of the present invention, which includes a broad molecular weight distribution, exhibits superior properties with respect to control J. Therefore, in one aspect of the present invention, by having a broad molecular weight distribution in the polypropylene composition that is subjected to melt spinning, superior cross-directional properties are obtained.

EXAMPLE 3

Fibers (2.2 dpf) are prepared using a two-step manufacturing process. Fiber spinning is carried out at 777 meters/minute using spinnerettes with 782 0.35 mm diameter holes. Fibers are crimped at 8–12 crimps/cm and cut into 3.8 cm long staple at a drawing speed of 120 meters/minute. Polymers II and IV of Example 1 are used. Fiber samples L and M are prepared using the formulations and conditions as set forth in the following Table 5. Fiber sample M is a example of the present invention, and fiber sample L is a control. Additives % are based on fiber weight.

TABLE 5

| Fiber Formulation | Spin Temp. °C.[1] | Draw Temp. °C.[2] |
|---|---|---|
| L polymer II<br>0.085% ULTRANOX 626<br>0.05% calcium stearate<br>0.1% TiO₂<br>0.008% LUPERSOL 101 | 285 | 60/60 |
| M 80% polymer II<br>20% polymer IV<br>0.085% ULTRANOX 626<br>0.05% calcium Stearate<br>0.1% TiO₂ | 305 | 60/60 |

[1]Extruder zones temperature.
[2]Feed-roll temperature/draw-roll temperature.

The fiber samples are tested and fabrics made and tested as in Example 1. Results are reported in the following Table 6. Again, the CD strength pertains to the fabric and the other results pertain to the fiber.

TABLE 6

| Sample | MFR | P.I. | Draw Ratio | % Elong | CD Strength |
|---|---|---|---|---|---|
| L | 26 | 4.2 | 1.2X | 372 | 410 |
| M | 20 | 5.4 | 1.2X | 506 | 600 |

Sample M of the present invention exhibits superior properties with respect to control L.

Although the invention has been described with reference to particular means, materials and embodiments, it is to be understood that the invention is not limited to the particulars disclosed and extends to all equivalents within the scope of the claims.

What is claimed:

1. A fiber comprising at least one substantially linear polypropylene having a melt flow rate of about 0.5–30, and at least one substantially linear polypropylene having a melt flow rate of about 60–1000.

2. The fiber according to claim 1, wherein, based on the weight of the fiber, said fiber comprises at least about 3.0% by weight of said at least one substantially linear polypropylene having a melt flow rate of about 0.5–30, and at least about 3.0% by weight of said at least one substantially linear polypropylene having a melt flow rate of about 60–1000.

3. The fiber according to claim 2, wherein, based on the weight of the fiber, said fiber comprises at least about 10.0% by weight of said at least one substantially linear polypropylene having a melt flow rate of about 0.5–30, and at least about 10.0% by weight of said at least one substantially linear polypropylene having a melt flow rate of about 60–1000.

4. The fiber according to claim 1, wherein said at least one substantially linear polypropylene having a melt flow rate of 0.5–30 comprises at least one substantially linear polypropylene having a melt flow rate of about 1–25, and said at least one substantially linear polypropylene having a melt flow rate of about 60–1000 comprises at least one substantially linear polypropylene having a melt flow rate of about 200–1000.

5. The fiber according to claim 4, wherein, based on the weight of the fiber, said fiber comprises at least about 3.0% by weight of said at least one substantially linear polypropylene having a melt flow rate of about 1–25, and at least about 3.0% by weight of said at least one substantially linear polypropylene having a melt flow rate of about 200–1000.

6. The fiber according to claim 5, wherein, based on the weight of the fiber, said fiber comprises at least about 10.0% by weight of said at least one substantially linear polypropylene having a melt flow rate of about 1–25, and at least about 10.0% by weight of said at least one substantially linear polypropylene having a melt flow rate of about 200–1000.

7. The fiber according to claim 1, wherein, based on the weight of the fiber, said at least one substantially linear polypropylene having a melt flow rate of about 0.5–30 is present in an amount of about 5–95%, and said at least one substantially linear polypropylene having a melt flow rate of about 60–1000 is present in an amount of about 5–95%.

8. The fiber according to claim 7, comprising about 2–5% by weight of substantially linear polypropylene having a melt flow rate of about 0.5–5, about 70–85% by weight of substantially linear polypropylene having a melt flow rate of about 10–20, and about 10–28% by weight of substantially linear polypropylene having a melt flow rate of about 300–600.

9. The fiber according to claim 8, comprising about 3% by weight of substantially linear polypropylene having a melt flow rate of about 0.8–5, about 75% by weight of substantially linear polypropylene having a melt flow rate of about 10–15, and about 22% by weight of substantially linear polypropylene having a melt flow rate of about 350–450.

10. The fiber according to claim 9, having a size less than about 5 dpf.

11. The fiber according to claim 1, having an average rheological polydispersity index of at least about 4.5.

12. The fiber according to claim 11, having an average rheological polydispersity index of at least about 5.0.

13. The fiber according to claim 12, having an average rheological polydispersity index of at least about 5.5.

14. The fiber according to claim 12, having an average rheological polydispersity index of about 5.0–7.0.

15. The fiber according to claim 1, having a viscoelastic constant of about 1.5–2.0.

16. The fiber according to claim 1, having a fiber elongation of at least about 250%.

17. The fiber according to claim 1, having a fiber tenacity less than about 2.5 g/denier.

18. The fiber according to claim 1, having a size less than about 5 dpf.

19. The fiber according to claim 1, further comprising at least one additive.

20. The fiber according to claim 19, wherein said at least one additive comprises at least one stabilizer.

21. The fiber according to claim 1, wherein said fiber has a substantially uniform morphology.

22. The fiber according to claim 1, wherein the fiber is substantially uniformly stainable with ruthenium tetroxide.

23. A composition comprising at least one substantially linear polypropylene having a melt flow rate of about 0.5–30, and at least one substantially linear polypropylene having a melt flow rate of about 60–1000.

24. The composition according to claim 23, wherein, based on the weight of the composition, said composition comprises at least about 3.0% by weight of said at least one substantially linear polypropylene having a melt flow rate of about 0.5–30, and at least about 3.0% by weight of said at least one substantially linear polypropylene having a melt flow rate of about 60–1000.

25. The composition according to claim 24, wherein, based on the weight of the composition, said composition comprises at least about 10.0% by weight of said at least one substantially linear polypropylene having a melt flow rate of about 0.5–30, and at least about 10.0% by weight of said at least one substantially linear polypropylene having a melt flow rate of about 60–1000.

26. The composition according to claim 23, wherein said at least one substantially linear polypropylene having a melt flow rate of 0.5–30 comprises at least one substantially linear polypropylene having a melt flow rate of about 1–25, and said at least one substantially linear polypropylene having a melt flow rate of about 60–1000 comprises at least one substantially linear polypropylene having a melt flow rate of about 200–1000.

27. The composition according to claim 26, wherein, based on the weight of the composition, said composition comprises at least about 3.0% by weight of said at least one substantially linear polypropylene having a melt flow rate of about 1–25, and at least about 3.0% by weight of said at least one substantially linear polypropylene having a melt flow rate of about 200–1000.

28. The composition according to claim 27, wherein, based on the weight of the composition, said composition comprises at least about 10.0% by weight of said at least one substantially linear polypropylene having a melt flow rate of about 1–25, and at least about 10.0% by weight of said at least one substantially linear polypropylene having a melt flow rate of about 200–1000.

29. The composition according to claim 23, comprising at least one substantially linear polypropylene having a melt flow rate of about 1–25, and at least one substantially linear polypropylene having a melt flow rate of about 200–1000.

30. The composition according to claim 23, having an average rheological polydispersity index of at least about 4.5.

31. The composition according to claim 30, having an average rheological polydispersity index of at least about 5.0.

32. The composition according to claim 31, having an average rheological polydispersity index of at least about 5.5.

33. The composition according to claim 31, having an average rheological polydispersity index of about 5.0–7.0.

34. The composition according to claim 23, further comprising at least one additive.

35. The composition according to claim 34, wherein said at least one additive comprises at least one stabilizer.

36. The composition according to claim 23, wherein, based on the weight of the composition, said at least one substantially linear polypropylene having a melt flow rate of about 0.5–30 is present in an amount of about 5–95%, and said at least one substantially linear polypropylene having a melt flow rate of about 60–1000 is present in an amount of about 5–95%.

37. The composition according to claim 36, comprising about 2–5% by weight of substantially linear polypropylene having a melt flow rate of about 0.5–5, about 70–85% by weight of substantially linear polypropylene having a melt flow rate of about 10–20, and about 10–28% by weight of substantially linear polypropylene having a melt flow rate of about 300–600.

38. The composition according to claim 37, comprising about 3% by weight of substantially linear polypropylene having a melt flow rate of about 0.8–5, about 75% by weight of substantially linear polypropylene having a melt flow rate of about 10–15, and about 22% by weight of substantially linear polypropylene having a melt flow rate of about 350–450.

39. The composition according to claim 38, further comprising at least one stabilizer.

40. A polypropylene fiber comprising a mixture of at least two components, said at least two components comprising at least one first component of substantially linear polypropylene having a melt flow rate of about 0.5–30, and at least one second component of substantially linear polypropylene having a melt flow rate of about 60–1000, and the fiber having an average melt flow rate of about 5–40.

41. The polypropylene fiber according to claim 40 having an average melt flow rate of about 10–30.

42. The polypropylene fiber according to claim 41 having an average melt flow rate of about 15–25.

43. A polypropylene fiber, said fiber having an average melt flow rate of about 5–40 and containing at least about 3.0% of at least one substantially linear polypropylene having a melt flow rate of about 200–1000.

44. The polypropylene fiber according to claim 43 containing at least about 10% of at least one substantially linear polypropylene having a melt flow rate of about 200–1000.

45. The polypropylene fiber according to claim 43 having an average melt flow rate of about 10–30.

46. The polypropylene fiber according to claim 45 having an average melt flow rate of about 15–25.

47. The polypropylene fiber according to claim 43, wherein said fiber has a substantially uniform morphology.

48. The polypropylene fiber according to claim 43, wherein the fiber is substantially uniformly stainable with ruthenium tetroxide.

49. The polypropylene fiber according to claim 43, wherein said fiber has a substantially uniform morphology, and said fiber is substantially uniformly stainable with ruthenium tetroxide.

50. A polypropylene fiber, said fiber having an average rheological polydispersity index of at least about 4.5, and containing at least about 3.0% of at least one substantially linear polypropylene having a melt flow rate of about 200–1000.

51. The polypropylene fiber according to claim 50 containing at least about 10% of at least one substantially linear polypropylene having a melt flow rate of 200–1000.

52. The polypropylene fiber according to claim 50, wherein said fiber has an average melt flow rate of about 5–40.

53. The polypropylene fiber according to claim 52 having an average melt flow rate of about 10–30.

54. The polypropylene fiber according to claim 53 having an average melt flow rate of about 15–25.

55. The polypropylene fiber according to claim 50 having an average rheological polydispersity index of at least about 5.0.

56. The polypropylene fiber according to claim 55 having an average rheological polydispersity index of at least about 5.5.

57. The polypropylene fiber according to claim 55, having an average rheological polydispersity index of about 5.0–7.0.

58. The polypropylene fiber according to claim 50, wherein said fiber has a substantially uniform morphology.

59. The polypropylene fiber according to claim 50, wherein the fiber is substantially uniformly stainable with ruthenium tetroxide.

60. The polypropylene fiber according to claim 50, wherein said fiber has a substantially uniform morphology, and said fiber is substantially uniformly stainable with ruthenium tetroxide.

61. A polypropylene fiber, said fiber having a zero shear viscosity of at least about $2.0 \times 10^4$ poise, and a viscoelastic constant of at least about 1.50.

62. A thermally bondable fiber produced by a process for spinning polypropylene filaments comprising:

melt spinning a polypropylene composition having a broad molecular weight distribution comprising at least one substantially linear polypropylene having a melt flow rate of about 0.5–30, and at least one substantially linear polypropylene having a melt flow rate of about 60–1000 through at least one spinnerette to form molten polypropylene filaments; and quenching the molten polypropylene filaments to obtain polypropylene filaments having an average rheological polydispersity index of at least about 5.0.

63. A thermally bondable fiber produced by a process for spinning polypropylene filaments comprising:

melt spinning a polypropylene composition having a broad molecular weight distribution through at least one spinnerette at a spinning speed of about 30 to 200 meters per minute to form molten polypropylene filaments; and quenching the molten polypropylene filaments.

64. A thermally bondable fiber produced by a process for producing thermobondable filaments having an average rheological polydispersity index of at least about 4.5 which is substantially maintained throughout the process, comprising:

melt spinning a polypropylene composition having a broad molecular weight distribution comprising at least one substantially linear polypropylene having a melt flow rate of about 0.5–30, and at least one substantially linear polypropylene having a melt flow rate of about 60–1000, and having an average rheological polydispersity index of at least about 4.5 through at least one spinnerette to form molten polypropylene filaments; and quenching the molten polypropylene filaments under conditions to obtain polypropylene filaments having an average rheological polydispersity index of at least about 4.5.

65. A thermally bondable fiber produced by a process for producing thermobondable filaments having an average rheological polydispersity index of at least about 4.5 which is substantially maintained throughout the process, comprising:

melt spinning a polypropylene composition having a broad molecular weight distribution comprising at least one substantially linear polypropylene having a melt flow rate of about 0.5–30, and at least one substantially linear polypropylene having a melt flow rate of about 60–1000, and having an average rheological polydispersity index of at least about 4.5 through at least one spinnerette to form molten polypropylene filaments; and quenching the molten polypropylene filaments under conditions to obtain a substantially uniform morphology of the quenched polypropylene filaments having an average rheological polydispersity index of at least about 4.5.

66. A thermally bondable fiber produced by a process for spinning polypropylene filaments comprising:

melt spinning a polypropylene composition having a broad molecular weight distribution through at least one spinnerette at a spinning speed of about 30 to 200 meters per minute to form molten polypropylene filaments; and quenching the molten polypropylene filaments to obtain polypropylene filaments having an average rheological polydispersity index of at least about 4.5.

67. A thermally bondable fiber produced by a process for spinning polypropylene filaments comprising:

melt spinning a polypropylene composition having a broad molecular weight distribution, and containing at least about 3.0% of at least one polypropylene having a melt flow rate of about 60–1000, through at least one spinnerette at a spinning speed of about 30 to 200 meters per minute to form molten polypropylene filaments; and quenching the molten polypropylene filaments to obtain polypropylene filaments having an average melt flow rate of about 5–40.

68. The polypropylene fiber according to claim 40, wherein said fiber has an average rheological polydispersity index of at least about 5.0.

69. The thermally bondable polypropylene fiber according to claim 68, having an average rheological polydispersity index of at least about 5.5.

70. The thermally bondable polypropylene fiber according to claim 68, having an average rheological polydispersity index of about 5.0–7.0.

71. The fiber according to claim 1, comprising a staple fiber.

72. The fiber according to claim 1, wherein said fiber has a denier per filament of about 0.5 to 3.0.

73. The fiber according to claim 1, comprising a staple fiber having a denier per filament of less than about 5.

74. The fiber according to claim 1, comprising a spun bond fiber.

75. The fiber according to claim 72, comprising a staple fiber.

76. The fiber according to claim 40, wherein said fiber has a denier per filament of less than about 5.

77. The fiber according to claim 40, comprising a staple fiber having a denier per filament of less than about 5.

78. The fiber according to claim 40, comprising a spun bond fiber.

79. The fiber according to claim 43, comprising a staple fiber.

80. The fiber according to claim 43, wherein said fiber has a denier per filament of less than about 5.

81. The fiber according to claim 43, comprising a staple fiber having a denier per filament of less than about 5.

82. The fiber according to claim 43, comprising a spun bond fiber.

83. The fiber according to claim 50, comprising a staple fiber.

84. The fiber according to claim 50, wherein said fiber has a denier per filament of less than about 5.

85. The fiber according to claim 50, comprising a staple fiber having a denier per filament of less than about 5.

86. The fiber according to claim 50, comprising a spun bond fiber.

87. The fiber according to claim 61, comprising a staple fiber.

88. The fiber according to claim 61, wherein said fiber has a denier per filament of less than about 5.

89. The fiber according to claim 61, comprising a staple fiber having a denier per filament of less than about 5.

90. The fiber according to claim 61, comprising a spun bond fiber.

91. The fiber according to claim 62, wherein, based on the weight of the composition, said composition comprises at least about 3.0% by weight of said at least one substantially linear polypropylene having a melt flow rate of about 0.5–30, and at least about 3.0% by weight of said at least one substantially linear polypropylene having a melt flow rate of about 60–1000.

92. The fiber according to claim 91, wherein, based on the weight of the composition, said composition comprises at least about 10.0% by weight of said at least one substantially linear polypropylene having a melt flow rate of about 0.5–30, and at least about 10.0% by weight of said at least one substantially linear polypropylene having a melt flow rate of about 60–1000.

93. The fiber according to claim 62, wherein said at least one substantially linear polypropylene having a melt flow rate of 0.5–30 comprises at least one substantially linear polypropylene having a melt flow rate of about 1–25, and said at least one substantially linear polypropylene having a melt flow rate of about 60–1000 comprises at least one substantially linear polypropylene having a melt flow rate of about 200–1000.

94. The fiber according to claim 63, wherein said polypropylene composition having a broad molecular weight distribution comprises at least one substantially linear polypropylene having a melt flow rate of about 0.5–30, and at least one substantially linear polypropylene having a melt flow rate of about 60–1000.

95. The fiber according to claim 94, wherein, based on the weight of the composition, said composition comprises at least about 3.0% by weight of said at least one substantially linear polypropylene having a melt flow rate of about 0.5–30, and at least about 3.0% by weight of said at least one substantially linear polypropylene having a melt flow rate of about 60–1000.

96. The fiber according to claim 95, wherein, based on the weight of the composition, said composition comprises at least about 10.0% by weight of said at least one substantially linear polypropylene having a melt flow rate of about 0.5–30, and at least about 10.0% by weight of said at least one substantially linear polypropylene having a melt flow rate of about 60–1000.

97. The fiber according to claim 94, wherein said at least one substantially linear polypropylene having a melt flow rate of 0.5–30 comprises at least one substantially linear polypropylene having a melt flow rate of about 1–25, and said at least one substantially linear polypropylene having a melt flow rate of about 60–1000 comprises at least one substantially linear polypropylene having a melt flow rate of about 200–1000.

98. The fiber according to claim 64, wherein, based on the weight of the composition, said composition comprises at least about 3.0% by weight of said at least one substantially linear polypropylene having a melt flow rate of about 0.5–30, and at least about 3.0% by weight of said at least one substantially linear polypropylene having a melt flow rate of about 60–1000.

99. The fiber according to claim 98, wherein, based on the weight of the composition, said composition comprises at least about 10.0% by weight of said at least one substantially linear polypropylene having a melt flow rate of about 0.5–30, and at least about 10.0% by weight of said at least one substantially linear polypropylene having a melt flow rate of about 60–1000.

100. The fiber according to claim 64, wherein said at least one substantially linear polypropylene having a melt flow rate of 0.5–30 comprises at least one substantially linear polypropylene having a melt flow rate of about 1–25, and said at least one substantially linear polypropylene having a melt flow rate of about 60–1000 comprises at least one substantially linear polypropylene having a melt flow rate of about 200–1000.

101. The fiber according to claim 65, wherein, based on the weight of the composition, said composition comprises at least about 3.0% by weight of said at least one substantially linear polypropylene having a melt flow rate of about 0.5–30, and at least about 3.0% by weight of said at least one substantially linear polypropylene having a melt flow rate of about 60–1000.

102. The fiber according to claim 101, wherein, based on the weight of the composition, said composition comprises at least about 10.0% by weight of said at least one substantially linear polypropylene having a melt flow rate of about 0.5–30, and at least about 10.0% by weight of said at least one substantially linear polypropylene having a melt flow rate of about 60–1000.

103. The fiber according to claim 65, wherein said at least one substantially linear polypropylene having a melt flow rate of 0.5–30 comprises at least one substantially linear polypropylene having a melt flow rate of about 1–25, and said at least one substantially linear polypropylene having a melt flow rate of about 60–1000 comprises at least one substantially linear polypropylene having a melt flow rate of about 200–1000.

104. The fiber according to claim 66, wherein said polypropylene composition having a broad molecular weight distribution comprises at least one substantially linear polypropylene having a melt flow rate of about 0.5–30, and at least one substantially linear polypropylene having a melt flow rate of about 60–1000.

105. The fiber according to claim 104, wherein, based on the weight of the composition, said composition comprises at least about 3.0% by weight of said at least one substantially linear polypropylene having a melt flow rate of about 0.5–30, and at least about 3.0% by weight of said at least one substantially linear polypropylene having a melt flow rate of about 60–1000.

106. The fiber according to claim 105, wherein, based on the weight of the composition, said composition comprises at least about 10.0% by weight of said at least one substantially linear polypropylene having a melt flow rate of about 0.5–30, and at least about 10.0% by weight of said at least one substantially linear polypropylene having a melt flow rate of about 60–1000.

107. The fiber according to claim 104, wherein said at least one substantially linear polypropylene having a melt flow rate of 0.5–30 comprises at least one substantially linear polypropylene having a melt flow rate of about 1–25, and said at least one substantially linear polypropylene having a melt flow rate of about 60–1000 comprises at least one substantially linear polypropylene having a melt flow rate of about 200–1000.

108. The fiber according to claim 67, wherein said polypropylene composition having a broad molecular weight distribution comprises at least one substantially linear polypropylene having a melt flow rate of about 0.5–30, and at least one substantially linear polypropylene having a melt flow rate of about 60–1000.

109. The fiber according to claim 108, wherein, based on the weight of the composition, said composition comprises at least about 3.0% by weight of said at least one substantially linear polypropylene having a melt flow rate of about 0.5–30, and at least about 3.0% by weight of said at least one substantially linear polypropylene having a melt flow rate of about 60–1000.

110. The fiber according to claim 109, wherein, based on the weight of the composition, said composition comprises at least about 10.0% by weight of said at least one substantially linear polypropylene having a melt flow rate of about 0.5–30, and at least about 10.0% by weight of said at least one substantially linear polypropylene having a melt flow rate of about 60–1000.

111. The fiber according to claim 108, wherein said at least one substantially linear polypropylene having a melt flow rate of 0.5–30 comprises at least one substantially linear polypropylene having a melt flow rate of about 1–25, and said at least one substantially linear polypropylene having a melt flow rate of about 60–1000 comprises at least one substantially linear polypropylene having a melt flow rate of about 200–1000.

112. The fiber according to claim 62, wherein said polypropylene composition comprises a polypropylene blend.

113. The fiber according to claim 94, wherein said polypropylene composition comprises a polypropylene blend.

114. The fiber according to claim 64, wherein said polypropylene composition comprises a polypropylene blend.

115. The fiber according to claim 65, wherein said polypropylene composition comprises a polypropylene blend.

116. The fiber according to claim 104, wherein said polypropylene composition comprises a polypropylene blend.

117. The fiber according to claim 108, wherein said polypropylene composition comprises a polypropylene blend.

* * * * *

UNITED STATES PATENT AND TRADEMARK OFFICE
CERTIFICATE OF CORRECTION

PATENT NO. : 5,629,080
DATED : May 13, 1997
INVENTOR(S) : Rakesh K. Gupta, James E. Mallory & Kunihiko Takeuchi It is certified that error appears in the above-indentified patent and that said Letters Patent is hereby corrected as shown below:

Claim 30, Column 16, Line 47 replace "theological" with --rheological--.

Signed and Sealed this

Twenty-first Day of October 1997

Attest:

BRUCE LEHMAN

*Attesting Officer*     *Commissioner of Patents and Trademarks*